(12) United States Patent
Yokoi et al.

(10) Patent No.: US 7,740,613 B2
(45) Date of Patent: Jun. 22, 2010

(54) INSERTER FOR AUTOMATICALLY INSERTING A CANNULA OF AN INDWELLING MEMBER OF AN INFUSION DEVICE

(75) Inventors: Hiroyuki Yokoi, Osaka (JP); Yukinori Ebara, Osaka (JP)

(73) Assignee: Nipro Corporation, Osaka (JP)

( * ) Notice: Subject to any disclaimer, the term of this patent is extended or adjusted under 35 U.S.C. 154(b) by 15 days.

(21) Appl. No.: 12/334,270

(22) Filed: Dec. 12, 2008

(65) Prior Publication Data
US 2010/0049129 A1  Feb. 25, 2010

(30) Foreign Application Priority Data
Aug. 20, 2008  (JP) .............................. 2008-211791

(51) Int. Cl.
*A61M 37/00* (2006.01)
*A61M 5/178* (2006.01)

(52) U.S. Cl. .............. 604/157; 604/164.08; 604/164.12

(58) Field of Classification Search ................. 604/134, 604/136, 137, 158, 162, 164.01, 164.08, 604/164.12, 165.01–165.03
See application file for complete search history.

(56) References Cited

U.S. PATENT DOCUMENTS

| 5,591,188 | A  | * | 1/1997 | Waisman ................. 606/182 |
| 5,851,197 | A  | * | 12/1998 | Marano et al. ............ 604/135 |
| 6,093,172 | A  |   | 7/2000 | Funderburk et al. |
| 6,991,619 | B2 |   | 1/2006 | Marano-Ford et al. |
| 6,991,620 | B2 | * | 1/2006 | Marano-Ford et al. ...... 604/157 |
| 6,997,907 | B2 | * | 2/2006 | Safabash et al. ............ 604/157 |
| 7,022,108 | B2 | * | 4/2006 | Marano-Ford et al. ...... 604/157 |
| 7,207,974 | B2 | * | 4/2007 | Safabash et al. ............ 604/136 |
| 7,585,287 | B2 | * | 9/2009 | Bresina et al. ........... 604/93.01 |
| 2005/0101912 | A1 |   | 5/2005 | Faust et al. |

FOREIGN PATENT DOCUMENTS

| WO | WO-99/33504 | A1 | 7/1999 |
| WO | WO-2005/046780 | A1 | 5/2005 |

* cited by examiner

*Primary Examiner*—Nicholas D Lucchesi
*Assistant Examiner*—Nathan R Price
(74) *Attorney, Agent, or Firm*—Birch, Stewart, Kolasch & Birch, LLP

(57) ABSTRACT

An inserter includes a housing, a plunger holding an indwelling member, a lifter contained in the housing in the state where the lifter is axially movable relative to the plunger, a needle holder contained in the housing and having a projection that can be latched by the plunger and the lifter, an insertion needle held by the needle holder and inserted in a cannula, and a spring provided between the plunger and the lifter and applying a biasing force in the direction of biasing the plunger and the lifter away from each other. The projection of the needle holder is latched by the plunger before the indwelling member reaches the body surface of the user, and latched by the lifter after the indwelling member reaches the body surface of the user.

5 Claims, 20 Drawing Sheets

INSERTER FOR AUTOMATICALLY INSERTING A CANNULA OF AN INDWELLING MEMBER OF AN INFUSION DEVICE

This nonprovisional application is based on Japanese Patent Application No. 2008-211791 filed on Aug. 20, 2008 with the Japan Patent Office, the entire contents of which are hereby incorporated by reference.

BACKGROUND OF THE INVENTION

1. Field of the Invention

The present invention relates to an inserter, and particularly to an inserter for inserting a cannula of an indwelling member of an infusion device into the body of a user who is to receive an injection (hereinafter simply referred to as "user").

2. Description of the Background Art

U.S. Pat. No. 6,093,172 (Patent Document 1) and International Patent Publication No. WO 99/033504 (Patent Document 2) each disclose an inserter having the capability of automatically inserting a part of an insertion set into the body of a patient by forcing a carrier body to move.

Further, U.S. Pat. No. 6,991,619 (Patent Document 3) discloses that a safety cover is attached to an insertion needle after a cannula of an inserter having an automatic insertion capability has been inserted.

Furthermore, U.S. Patent Publication No. 2005/0101912 (Patent Document 4) and International Patent Publication No. WO 2005/046780 (Patent Document 5) each disclose an inserter having the capability of automatically retracting a cannula of a subcutaneous infusion device.

As for the inserters disclosed in patent Documents 1 and 2, an insertion needle is exposed when the inserter is removed after inserted. Accordingly, there is a possibility that the tip of the used insertion needle punctures a finger of the user (this puncture is herein referred to as "accidental puncture"). While patent Document 3 attaches the safety cover to the insertion needle, accidental puncture could still occur when the safety cover is attached.

Further, the inserters disclosed in Patent Documents 4 and 5 each lack the capability of automatically inserting the cannula. Therefore, manual insertion is necessary which could make the user feel dangerous.

SUMMARY OF THE INVENTION

An object of the present invention is to provide an inserter that can automatically insert a cannula of an infusion device while suppressing accidental puncture by an insertion needle.

An inserter according to the present invention is used for automatically inserting a cannula of an indwelling member of an infusion device into a body of a user, and includes: a tubular housing; a first member contained in the housing in a state where the first member is movable in an axial direction and holding the indwelling member; a second member provided on a side opposite to a body surface of the user with respect to the first member, contained in the housing in a state where the second member is relatively movable in the axial direction relative to the first member, and having a first latch portion that can be latched by the housing; a third member contained in the housing and having a second latch portion that can be latched by the first member and the second member; an insertion needle held by the third member and inserted in the cannula; and a biasing member provided between the first member and the second member and applying a biasing force in a direction of biasing the first member and the second member away from each other. Before the indwelling member reaches the body surface of the user, the first latch portion of the second member is latched by the housing and the second latch portion of the third member is latched by the first member. A latch release portion is provided that releases latching of the first latch portion of the second member by the housing when the indwelling member reaches the body surface of the user. A latch switch portion is provided that releases latching of the second latch portion of the third member by the first member when the indwelling member reaches the body surface of the user and causes the second latch portion of the third member to be latched by the second member.

"Latch" herein refers to the state where two members abut on each other in such a manner that prevents the members from axially moving relative to each other.

The inserter having the above-described structure operates in the following way. Specifically, when automatic insertion of the indwelling member is started, the biasing force of the biasing member biases the first member and the second member in the direction of biasing the first and second members away from each other. Here, before the indwelling member reaches the body surface of the user, the first latch portion of the second member is latched by the housing. Therefore, the second member does not move while the first member holding the indwelling member moves toward the body surface of the user. In this way, the automatic insertion of the cannula by means of the biasing force of the biasing member is performed. Then, when the indwelling member reaches the body surface of the user, the latching of the first latch portion of the second member by the housing and the latching of the second latch portion of the third member by the first member are released, while the second latch portion of the third member is latched by the second member. Here, the indwelling member has reached the body surface of the user, and accordingly the first member holding the indwelling member receives a reaction force from the body surface of the user so that the first member is fixed. In contrast, the latching of the second member by the housing is released so that the second member is movable. Therefore, the second member moves in the direction away from the body surface of the user. Here, the third member is latched by the second member and accordingly the third member is moved in the direction away from the body surface of the user together with the insertion needle and retracted into the housing. In this way, the automatic retraction of the insertion needle by means of the biasing force of the biasing member is performed.

The inserter in the present embodiment has, as described above, the capability of automatically inserting the cannula and the capability of automatically retracting the insertion needle, so that both of the advantage of facilitating the insertion of the cannula by the user and the advantage of suppressing accidental puncture by the insertion needle can be achieved. Further, the above-described automatic insertion capability and automatic retraction capability can be accomplished with a common spring and thus the inserter that is convenient to use can be provided while avoiding an increase of the number of parts.

According to an embodiment, in the inserter described above, the second member has a flange portion, the housing has a flange abutting portion abutting on a rim of the flange portion, the first member has a press portion pressing the flange abutting portion radially outward when the indwelling member reaches the body surface of the user, the first latch portion includes the flange portion, and the latch release portion includes the press portion.

According to an embodiment, in the inserter described above, the third member has a projection that protrudes radially outward and can be latched by the first member, and a taper portion whose diameter gradually decreases from an upper side toward a lower side, the second member has a taper abutting portion abutting on the taper portion when the indwelling member reaches the body surface of the user to deform the third member such that the projection is moved radially inward, the second latch portion includes the projection, and the latch switch portion includes the taper abutting portion.

According to an embodiment, in the inserter described above, the taper abutting portion of the second member latches the projection of the third member.

According to an embodiment, in the inserter described above, a lock mechanism is provided that is disposed on a side surface of the housing and locks the first member on the housing against the biasing force of the biasing member, and the lock mechanism is released by pressing a button protruding from the side surface of the housing.

In accordance with the present invention, an inserter can be provided that can automatically insert a cannula of an infusion device while suppressing accidental puncture by an insertion needle.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
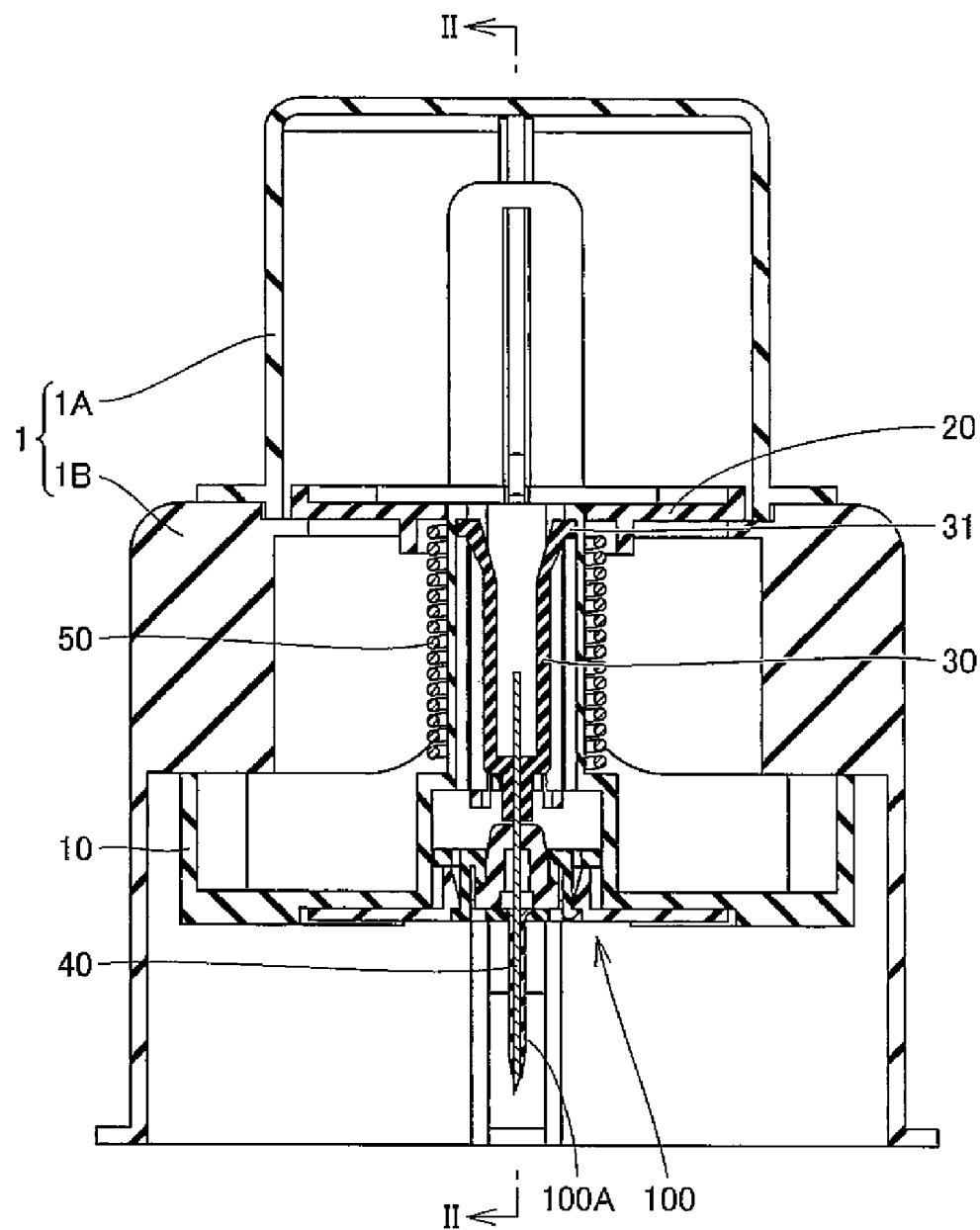
FIG. 1 is a cross-sectional view showing an inserter according to an embodiment of the present invention.

In the following, embodiments of the present invention will be described. Here, like or corresponding components are denoted by like reference characters and a description thereof may not be repeated in some cases.

It should be noted that, in the embodiments described below where a certain number of components, a certain quantity or the like is specified, the scope of the present invention is not necessarily limited to the specified number or quantity unless otherwise stated. Further, in the following embodiments, each component is not necessarily requisite for the present invention unless otherwise stated.

Figure 2:
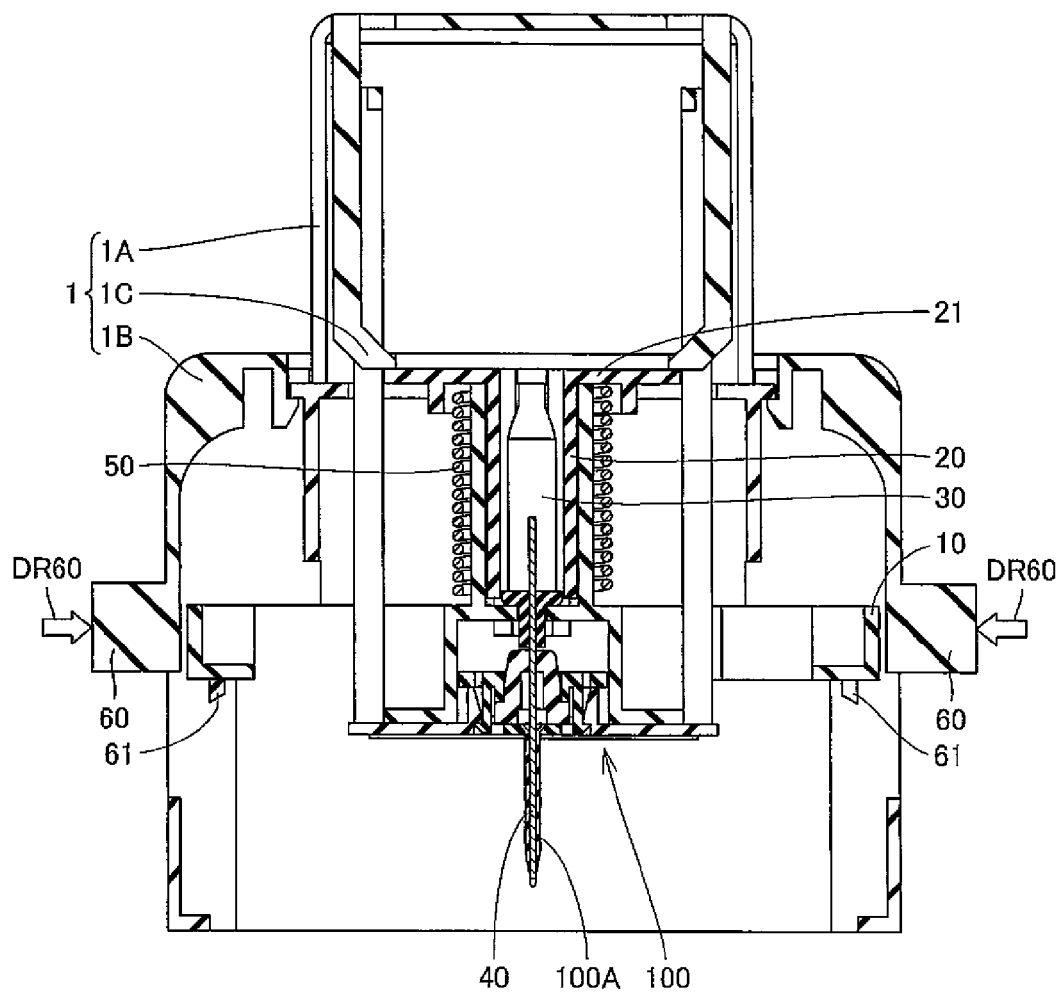
FIG. 2 is a cross-sectional view corresponding to the II-II cross section in FIG. 1.
Figure 3:
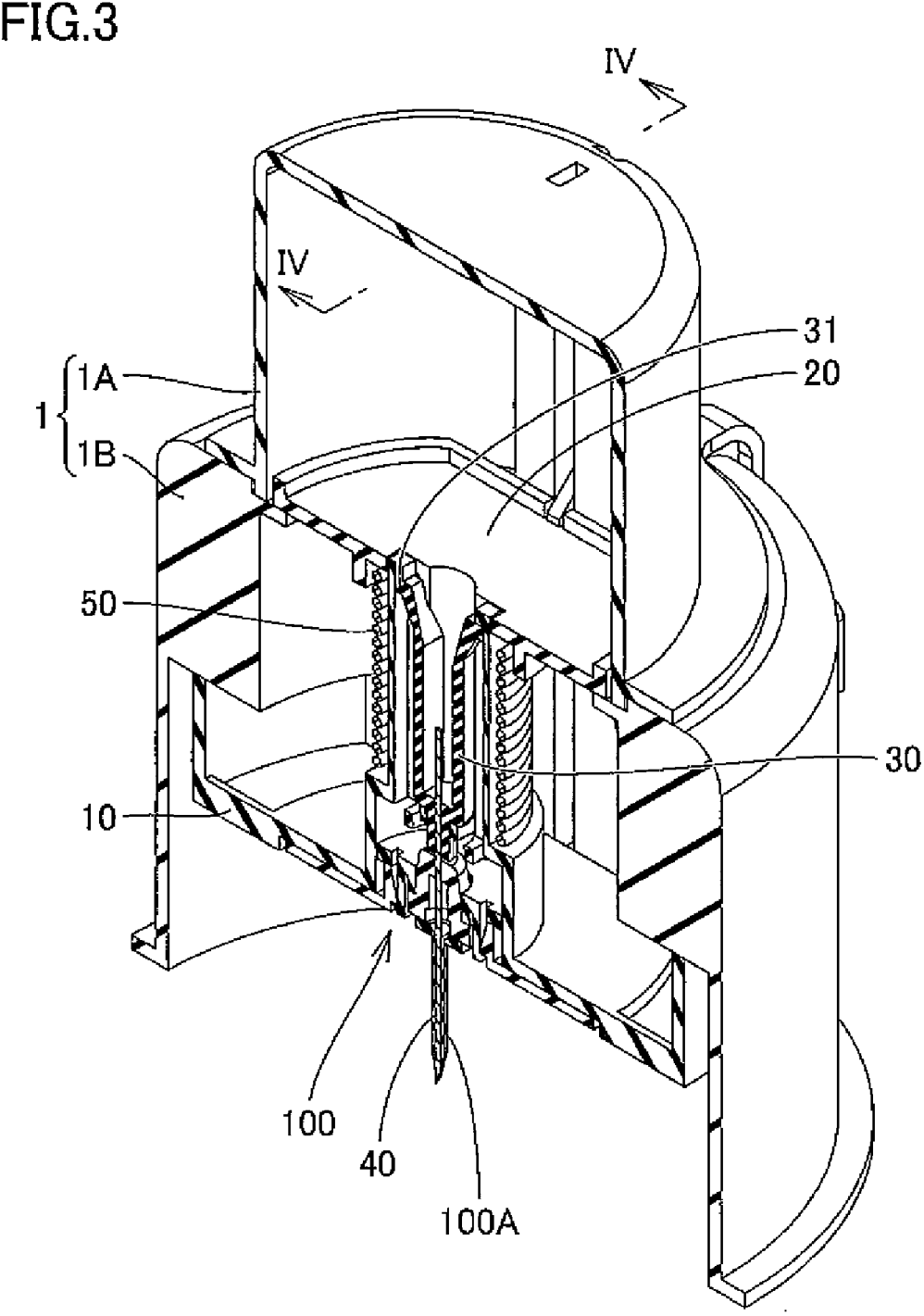
FIG. 3 is a perspective cross-sectional view showing the inserter according to an embodiment of the present invention.
Figure 4:
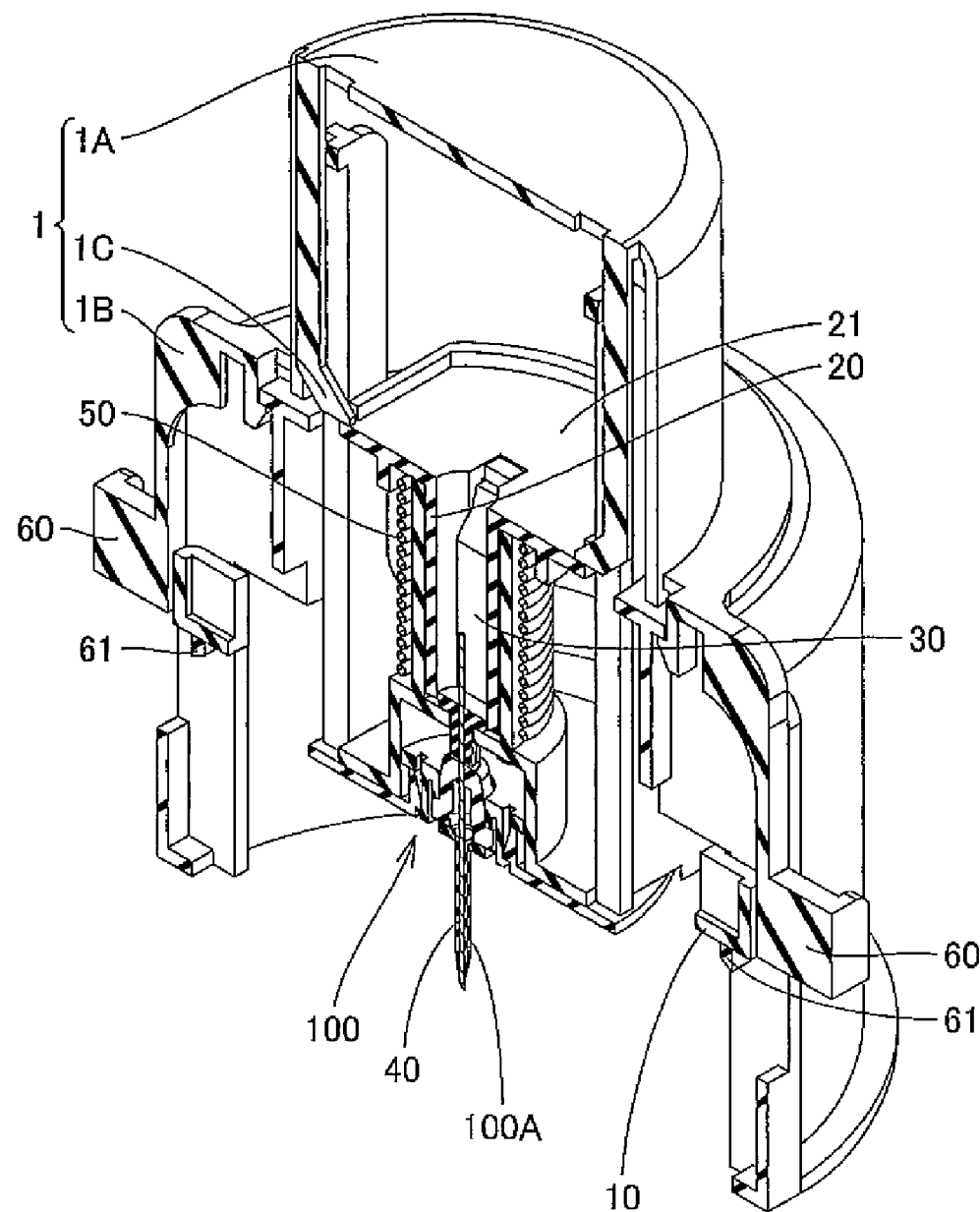
FIG. 4 is a perspective cross-sectional view corresponding to the IV-IV cross section in FIG. 3.

FIG. 1 is a cross-sectional view showing an inserter according to an embodiment of the present invention, and FIG. 2 is a cross-sectional view corresponding to the II-II cross section in FIG. 1. FIG. 3 is a perspective cross-sectional view showing this inserter, and FIG. 4 is a perspective cross-sectional view corresponding to the IV-IV cross section in FIG. 3.

The inserter in the present embodiment is an inserter for automatically inserting a cannula of an infusion device into the body of a user. The inserter includes as shown in FIGS. 1 to 4 a housing 1, a plunger 10, a lifter 20, a needle holder 30, an insertion needle 40, a spring 50, and an unlock portion 60.

Housing 1 is a member having the shape of a bottomed cylinder, and includes an upper member 1A and a lower member 1B. Here, upper member 1A and lower member 1B may be integrated into one unit. Upper member 1A has, at a position corresponding to an arm portion 11 described hereinlater of plunger 10, a pair of arms that are integrally provided. The upper ends of the arms are connected to the ceiling plate of upper member 1A, and the lower ends thereof are free ends. At the lower ends each, a projection 1C is formed. Projection 1C is a portion protruding from the radial outside toward the radial inside. The above-described arms formed at upper member 1A of housing 1 are configured to be deformable so that projection 1C is moved radially outward. In other words, the material and the thickness of the arms are appropriately adjusted.

Plunger 10 is contained in housing 1 in the state where the plunger is movable in the axial direction (up-and-down direction in FIGS. 1 to 4). Plunger 10 detachably holds indwelling member 100. Plunger 10 is biased toward the body surface of the user so that cannula 100A of indwelling member 100 is automatically inserted into the body of the user.

Lifter 20 is provided on the side opposite to the body surface of the user with respect to plunger 10. Lifter 20 is contained in housing 1 in the state where the lifter is relatively movable in the axial direction relative to plunger 10. Lifter 20 has a flange portion 21. Flange portion 21 abuts on projection 1C which is integrally formed with upper member 1A of housing 1, and is accordingly latched. In other words, projection 1C abuts on the outer rim of flange portion 21 to latch the flange portion so that lifter 20 is prevented from moving upward. Lifter 20 is a member for moving insertion needle 40 upward (in the direction away from the body of the user) after cannula 100A is automatically inserted.

Needle holder 30 is contained in housing 1 and holds insertion needle 40 in a fixed state. Needle holder 30 has a projection 31. Projection 31 is formed in such a manner that allows the projection to be latched by plunger 10 and lifter 20. The state where projection 31 is latched by plunger 10 and lifter 20 will be described hereinlater.

Insertion needle 40 held by needle holder 30 is a metal member inserted in cannula 100A. Insertion needle 40 serves as a core material when cannula 100A is inserted. Before cannula 100A is automatically inserted, the tip of insertion needle 40 is contained in housing 1. Accordingly, accidental puncture by insertion needle 40 is prevented.

Spring 50 is disposed between plunger 10 and lifter 20 in the state where a compression force is applied to the spring. Accordingly, plunger 10 and lifter 20 are biased in the direction of biasing plunger 10 and lifter 20 away from each other. At least a part of plunger 10, lifter 20 and needle holder 30 each is inserted in spring 50.

Housing 1, plunger 10, lifter 20 and needle holder 30 are each made of a thermoplastic resin such as polypropylene, polyethylene, polystyrene, acrylonitrile-styrene-butadiene copolymer synthetic resin, polycarbonate, polyethylene terephthalate, polybutylene terephthalate, polyacetal, polyamide) or methacrylate resin for example. In contrast, spring 50 is made of a metal such as SUS304WPB or SWP-A for example.

The elastic coefficient of spring 50 is appropriately changed. If the elastic coefficient is excessively small, however, puncture is difficult to accomplish. Further, in terms of a relation with the strength of housing 1 and plunger 10 for example, the upper limit of the elastic coefficient is defined. An example of the range of the elastic coefficient is approximately from not less than 0.02 N/mm to not more than 0.2 N/mm.

In the state shown in FIGS. 1 to 4, flange portion 21 of lifter 20 is latched by housing 1 and projection 31 of needle holder 30 is latched by plunger 10.

The inserter in the present embodiment is provided with a lock portion 61 serving as "lock mechanism" on the side surface of housing 1 as shown in FIGS. 2 and 4. Lock portion 61 locks plunger 10 on housing 1 against a biasing force of spring 50. Further, on the side surface of housing 1, an unlock portion 60 (button) protruding radially outward is also provided.

Figure 5:
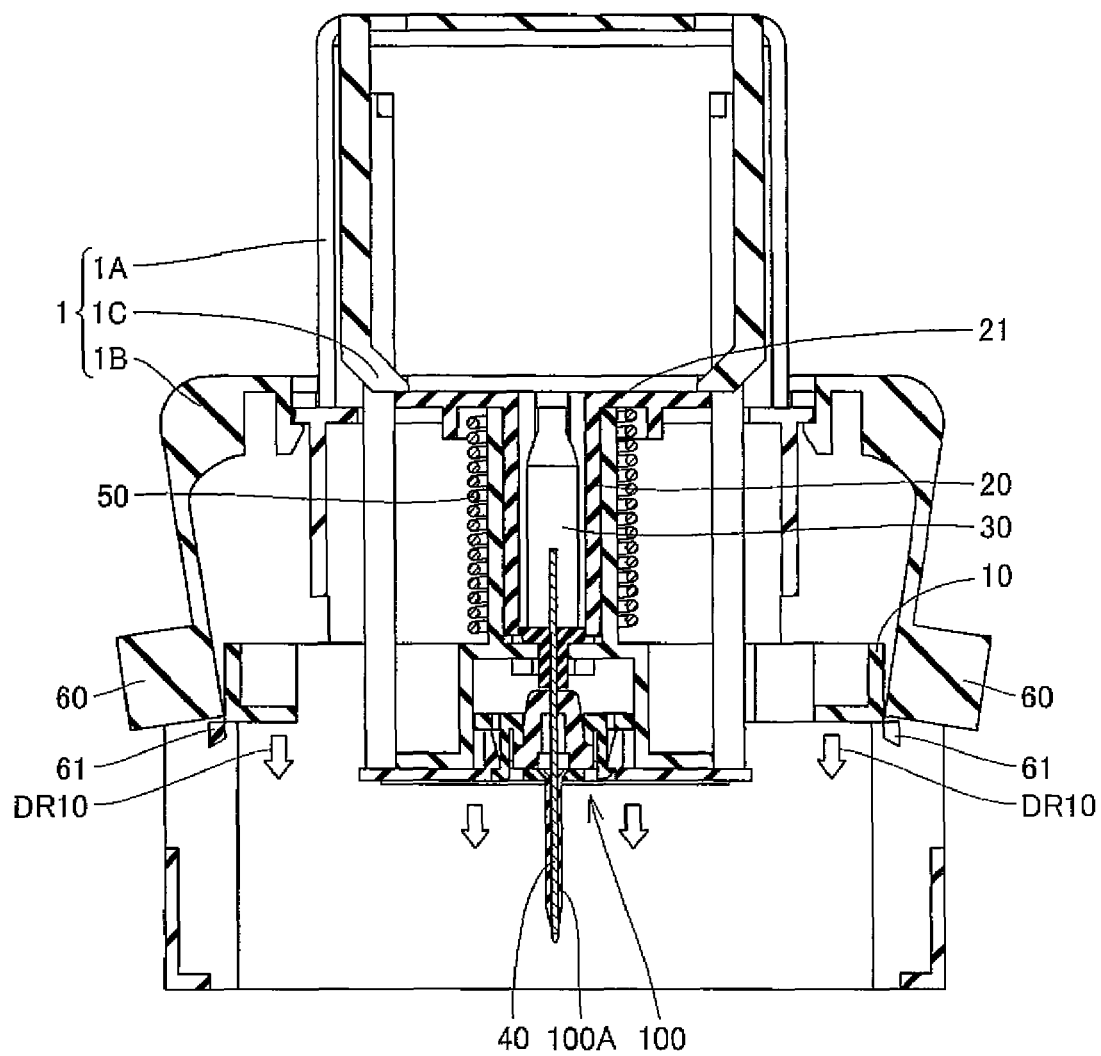
FIG. 5 is a cross-sectional view showing a first stage (unlocking) of an operation of the inserter shown in FIGS. 1 to 4.

In the following, an operation of the inserter in the present embodiment will be described. FIG. 5 is a cross-sectional view showing a stage where locking of the plunger is released in the operation of the inserter. As shown in FIG. 5, unlock portion 60 is pressed in the direction indicated by arrow DR60 (see FIG. 2) so that plunger 10 is deformed to cause a portion that is a part of the plunger 10 and that is latched by lock portion 61 to move radially inward, and accordingly the locking of plunger 10 by lock portion 61 is released. As a result, automatic insertion of indwelling member 100 is started.

The automatic insertion of indwelling member 100 is accomplished by the following mechanism. Specifically, when the locking of plunger 10 by lock portion 61 is released, the biasing force of spring 50 biases plunger 10 and lifer 20 in the direction of biasing the plunger and lifter away from each other. Here, flange portion 21 of lifter 20 is latched by projection 1C of housing 1 and thus lifter 20 cannot move upward. Therefore, the biasing force of spring 50 moves plunger 10 in the direction indicated by arrow DR10.

Figure 6:
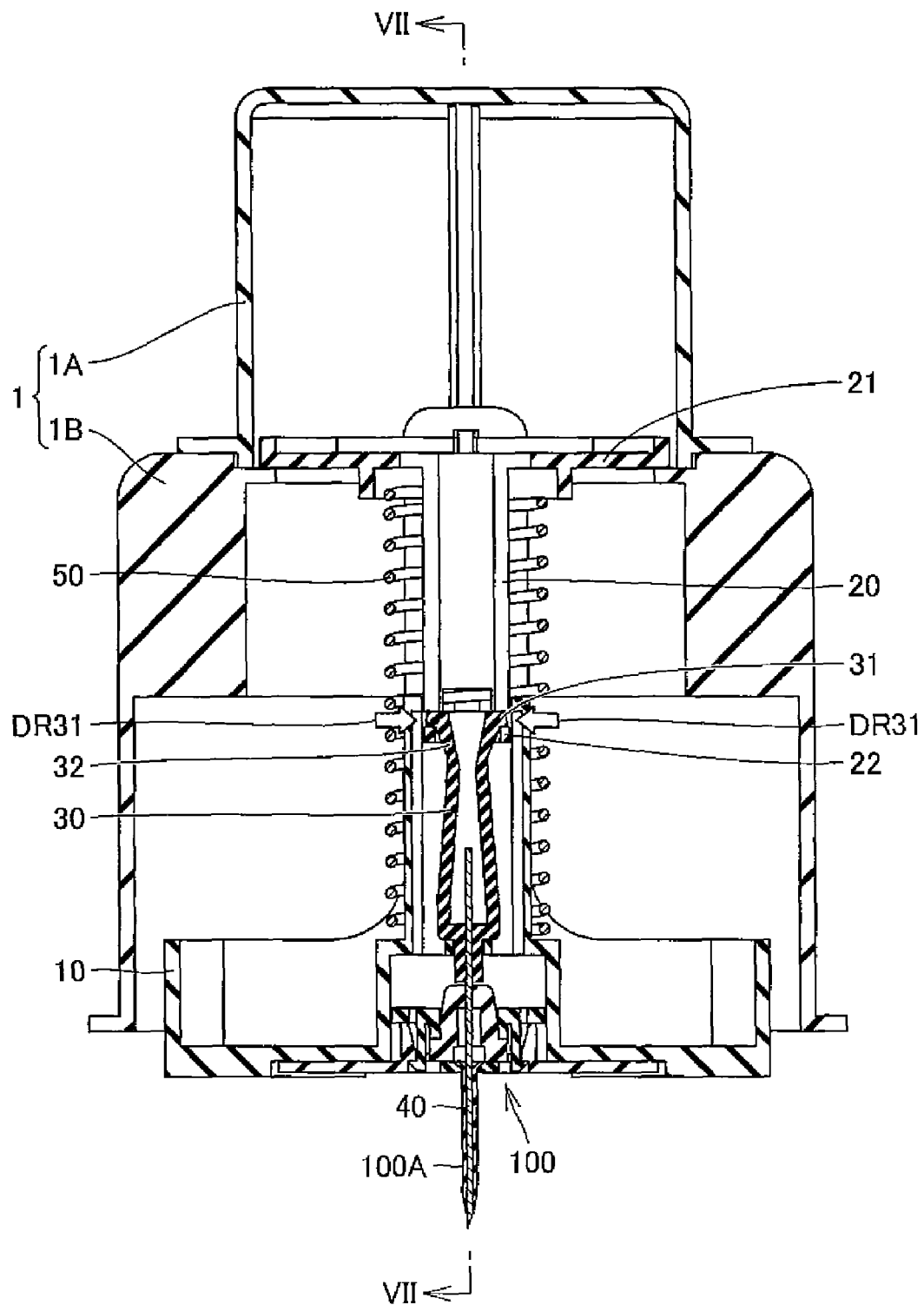
FIG. 6 is a cross-sectional view showing a second stage (insertion) of the operation of the inserter shown in FIGS. 1 to 4.

FIG. 6 is a cross-sectional view showing the state where the insertion in the operation of the inserter as described above is completed, and FIG. 7 is a cross-sectional view corresponding to the VII-VII cross section in FIG. 6. The bottom surface of plunger 10 slightly protrudes from the lower end of housing 1 in FIGS. 6 and 7, since the biasing force of spring 50 causes a part of the body surface abutting on plunger 10 to be slightly depressed.

Figure 7:
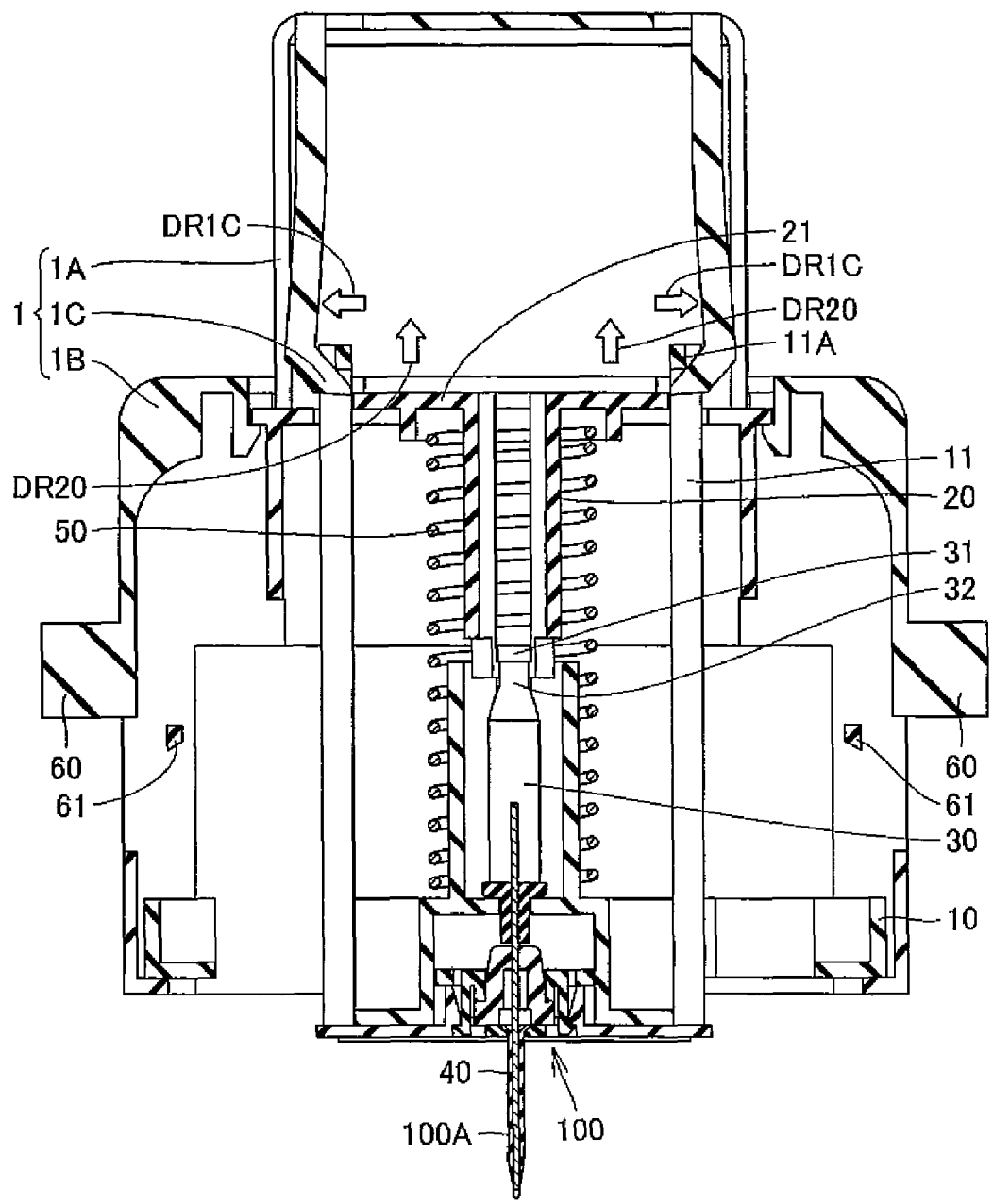
FIG. 7 is a cross-sectional view corresponding to the VII-VII cross section in FIG. 6.

Referring to FIGS. 6 and 7, plunger 10 includes arm portion 11 extending upward from the rim of the bottom surface and a hook portion 11A provided at the head of arm portion 11. When the bottom surface of plunger 10 and indwelling member 100 reach the body surface of the user, hook portion 11A abuts on projection 1C of housing 1 to move projection 1C radially outward (the direction indicated by arrow DR1C). Accordingly, the latching of flange portion 21 of lifter 20 by housing 1 is released. As a result, lifter 20 can move upward (the direction indicated by arrow DR20).

Further, needle holder 30 has a tapered surface 32 under projection 31. Tapered surface 32 extends to incline from the upper side to the lower side in the direction from the radial outside toward the radial inside. Specifically, the portion of needle holder 30 where tapered surface 32 is formed gradually decreases in diameter from the upper side to the lower side. Lifter 20 has a hook portion 22 at the lower end of the lifter. Hook portion 22 is located on the radial inside of the portion of plunger 10 that latches needle holder 30. The width of hook portion 22 is made smaller than the width of projection 31 of needle holder 30 in the state where the projection is latched by plunger 10. Therefore, hook portion 22 in the state shown in FIGS. 6 and 7 abuts on tapered surface 32 located under projection 31 to deform needle holder 30 so that projection 31 moves radially inward (the direction indicated by arrow DR31). Accordingly, the latching of projection 31 of needle holder 30 by plunger 10 is released. Projection 31 is then latched by hook portion 22. As a result, needle holder 30 is separated from plunger 10 and can move upward (the direction indicated by arrow DR20) together with lifter 20.

Figure 8:
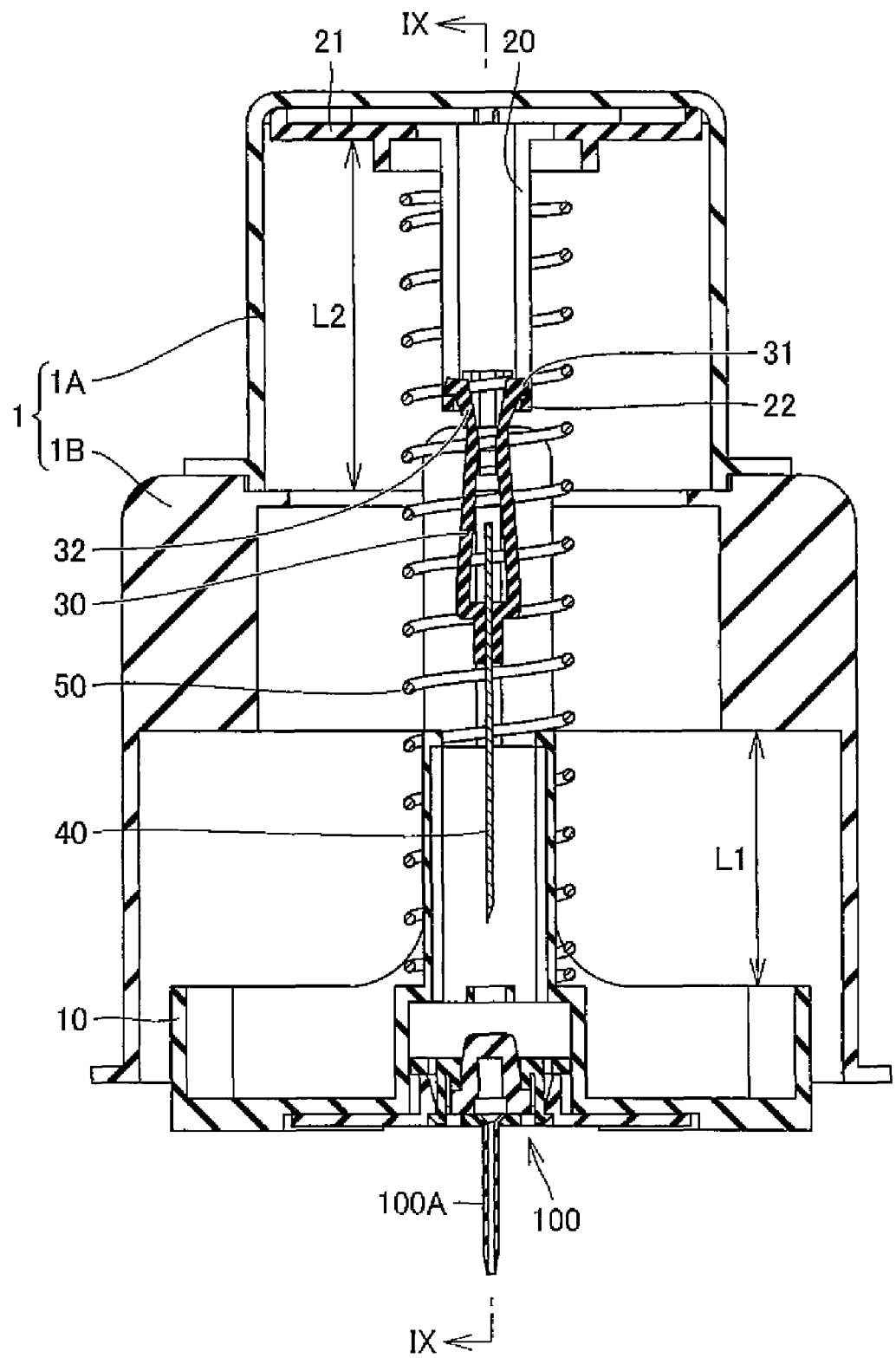
FIG. 8 is a cross-sectional view showing a third stage (retraction) of the operation of the inserter shown in FIGS. 1 to 4.
Figure 9:
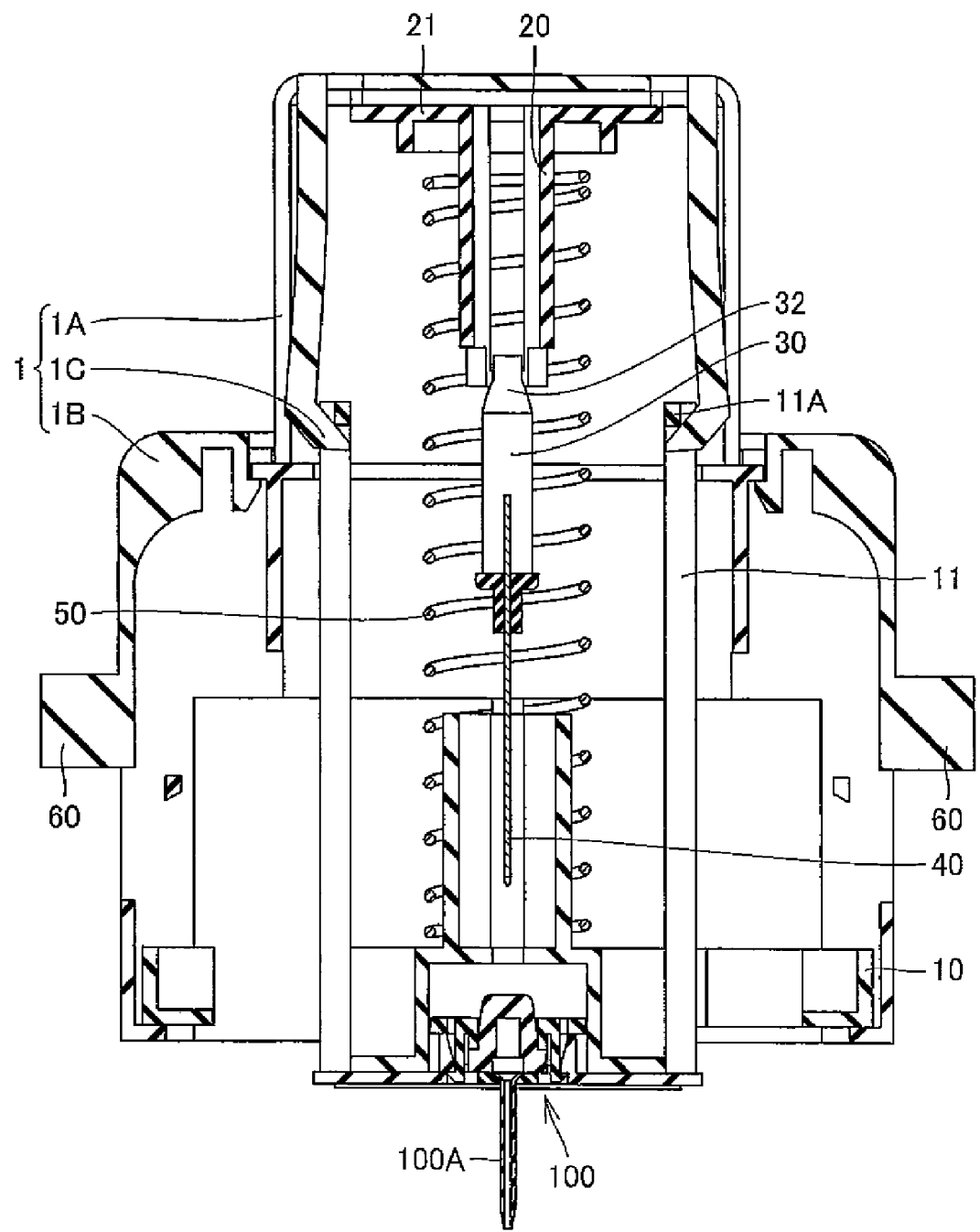
FIG. 9 is a cross-sectional view corresponding to the IX-IX cross section in FIG. 8.
Figure 10:
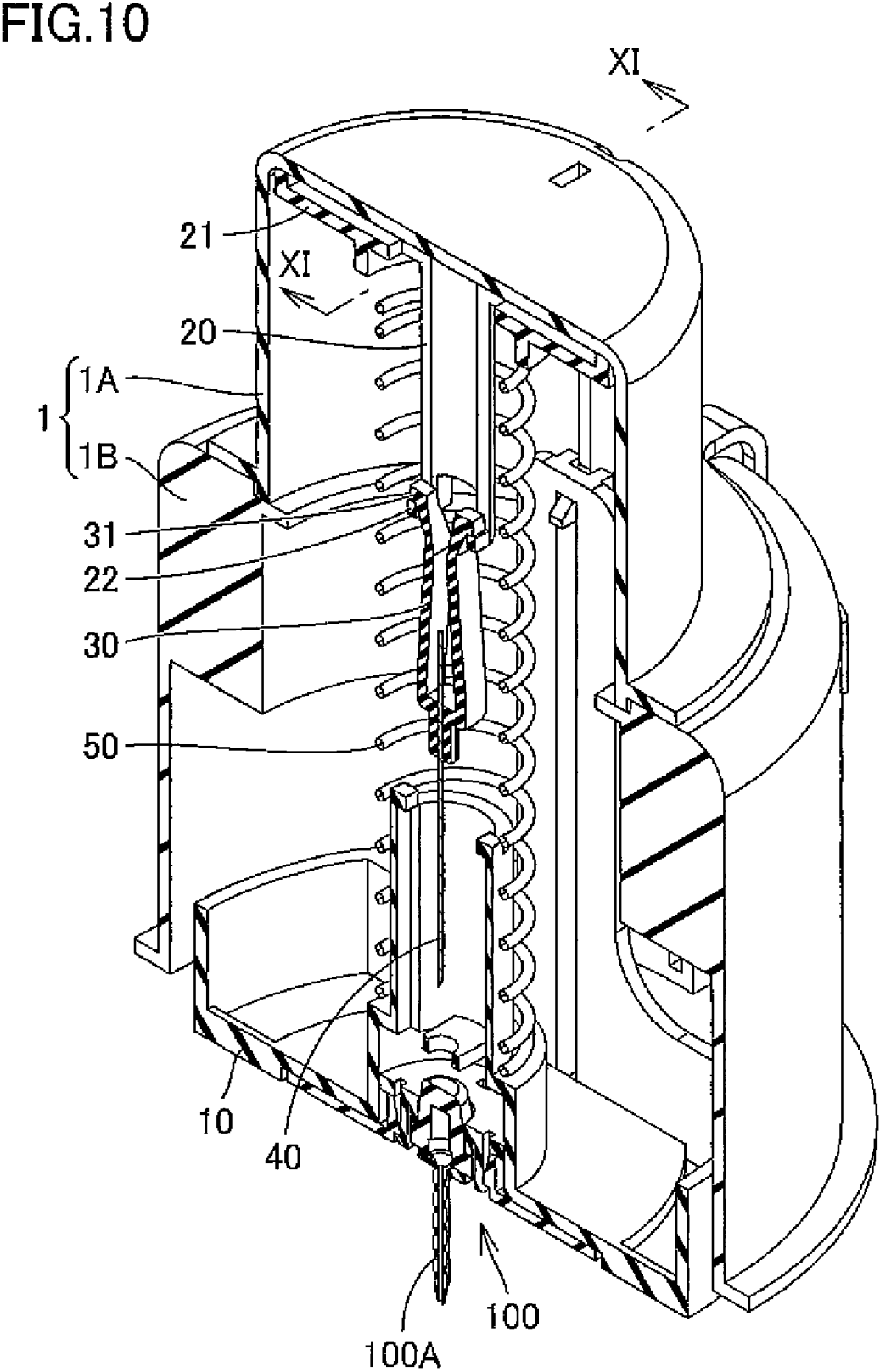
FIG. 10 is a perspective cross-sectional view showing the third stage (retraction) of the operation of the inserter shown in FIGS. 1 to 4.
Figure 11:
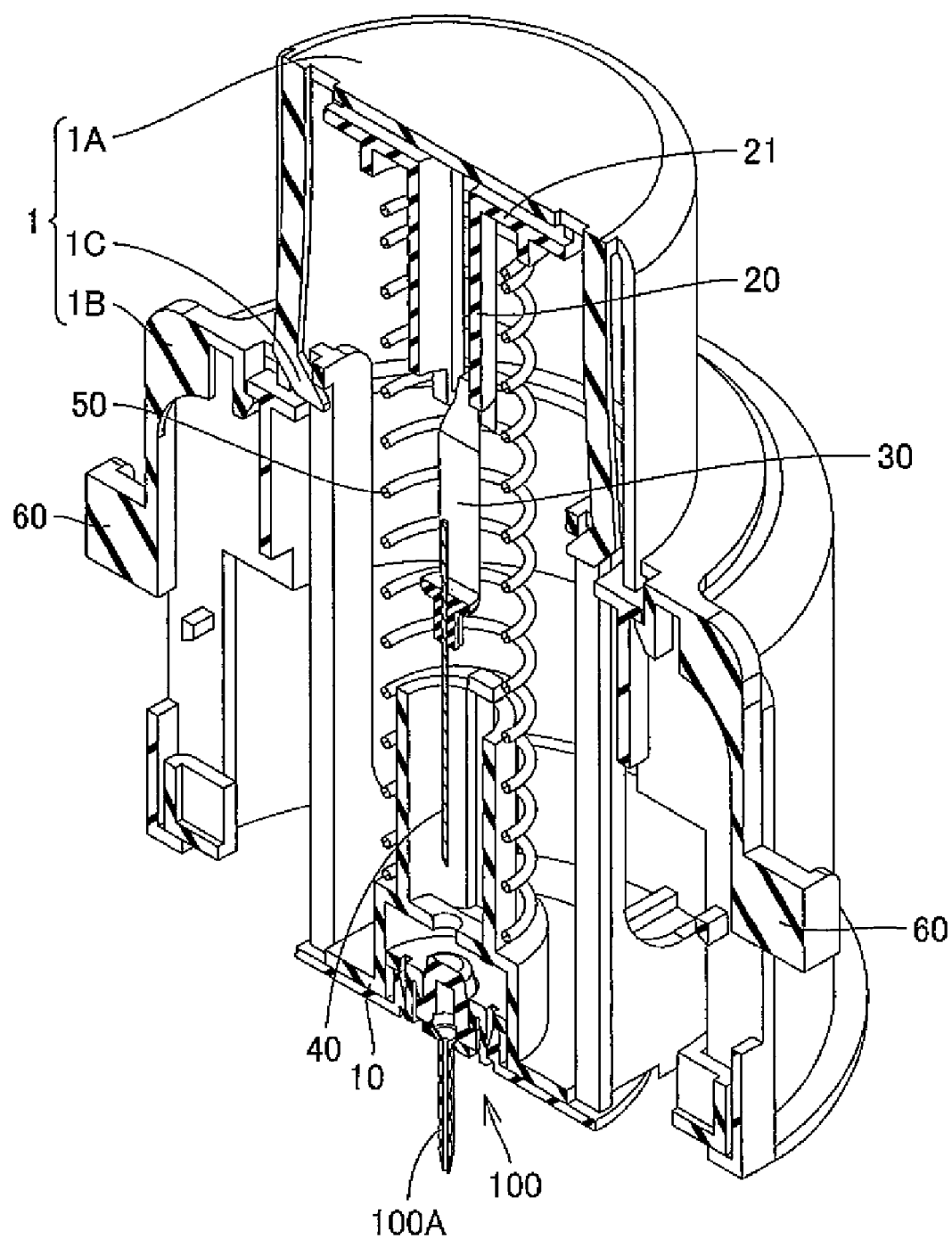
FIG. 11 is a perspective cross-sectional view corresponding to the XI-XI cross section in FIG. 10.

FIG. 8 is a cross-sectional view showing the state where retraction is completed in the operation of the inserter as described above and FIG. 9 is a cross-sectional view corresponding to the IX-IX cross section in FIG. 8. FIG. 10 is a perspective cross-sectional view showing the state in FIG. 8, and FIG. 11 is a perspective cross-sectional view corresponding to the XI-XT cross section in FIG. 10.

Referring to FIGS. 8 to 11, in the state where the bottom surface of plunger 10 and indwelling member 100 reach the body surface of the user, plunger 10 receives a reaction force from the body surface of the user and is accordingly fixed. In contrast, the latching of lifter 20 by housing 1 has been released and accordingly lifter 20 is movable. Thus, the biasing force of spring 50 moves lifter 20 in the direction away from the body surface of the user. Here, since needle holder 30 is latched by lifter 20, needle holder 30 also moves in the direction away from the body surface of the user, together with insertion needle 40. In this way, insertion needle 40 is automatically retracted by means of the biasing force of spring 50. In the present embodiment, relative to the amount of movement (L1) in the downward direction of plunger 10 when cannula 100A is automatically inserted, the amount of movement (L2) in the upward direction of lifter 20 and needle holder 30 when insertion needle 40 is automatically retracted is set larger. Therefore, insertion needle 40 held by needle holder 30 is completely retracted to be received within housing 1 by the above-described automatic retraction.

Figure 12:
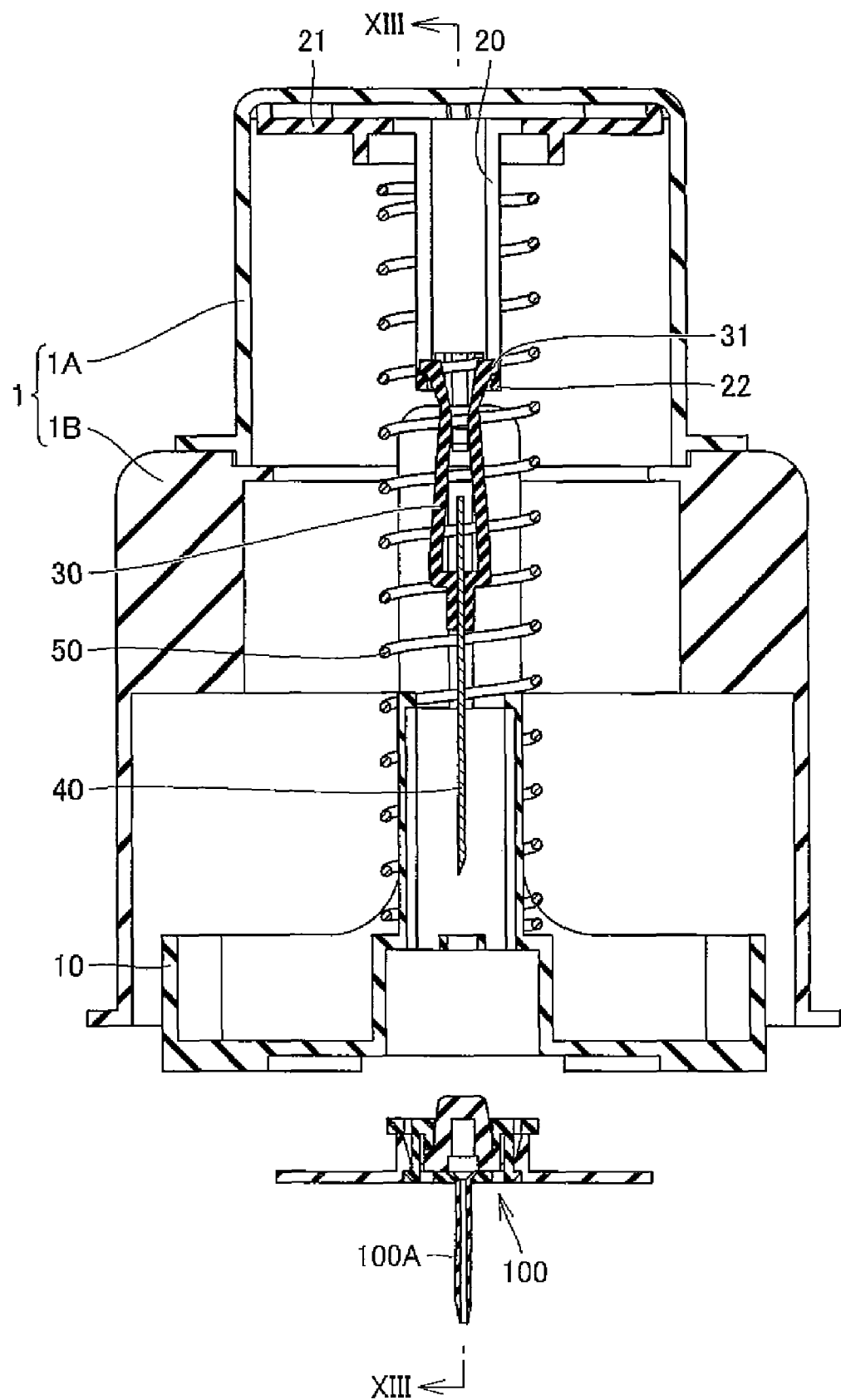
FIG. 12 is a cross-sectional view showing a fourth stage (inserter removal) of the operation of the inserter shown in FIGS. 1 to 4.
Figure 13:
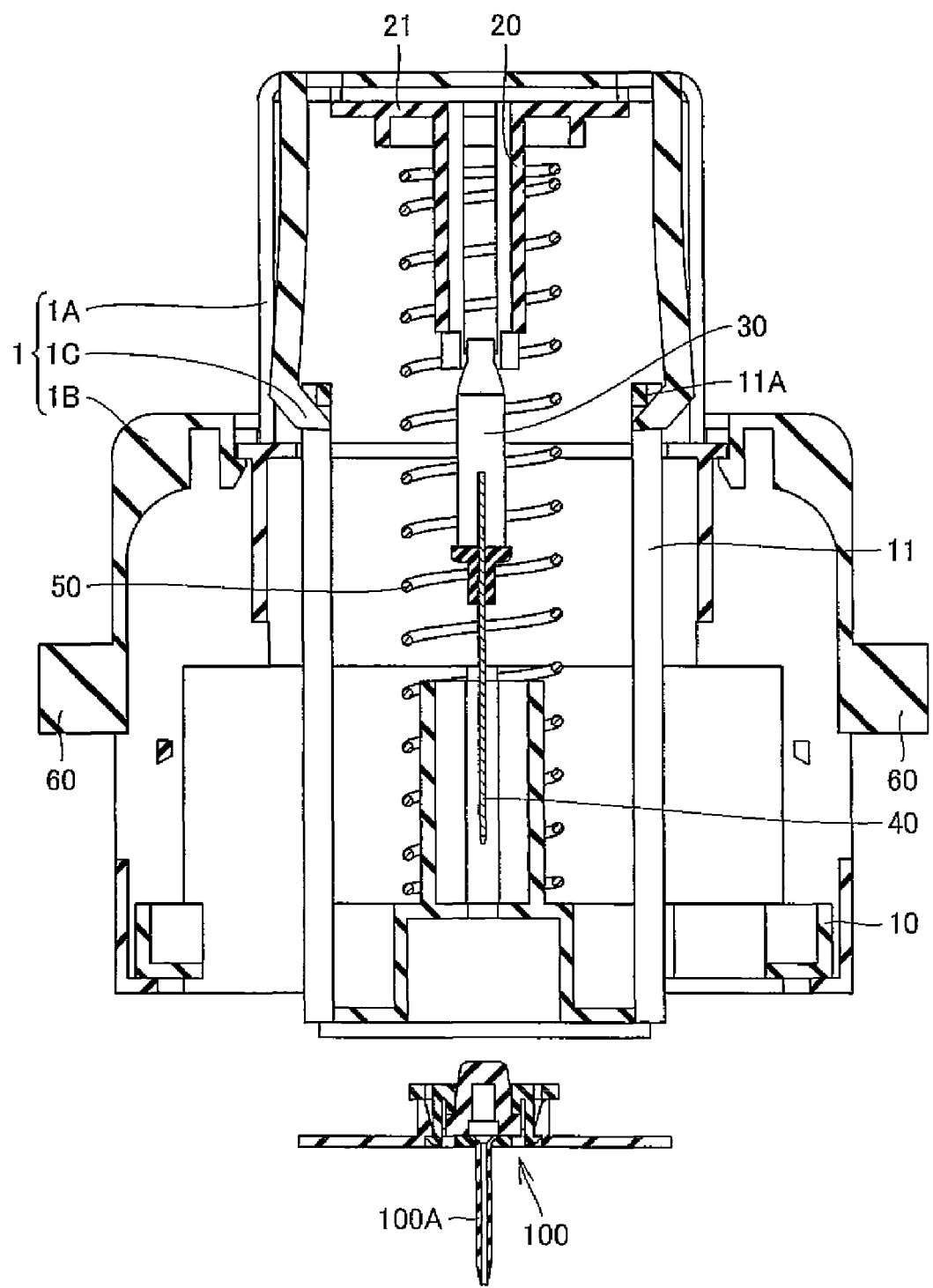
FIG. 13 is a cross-sectional view corresponding to the XIII-XIII cross section in FIG. 12.

FIG. 12 is a cross-sectional view showing the stage where the inserter is removed in the operation of the inserter as described above, and FIG. 13 is a cross-sectional view corresponding to the XIII-XIII cross section in FIG. 12. Referring to FIGS. 12 and 13, in the stage of removing the inserter after the insertion of cannula 100A is completed, insertion needle 40 is contained in housing 1 and thus accidental puncture by insertion needle 40 is suppressed.

Figure 14:
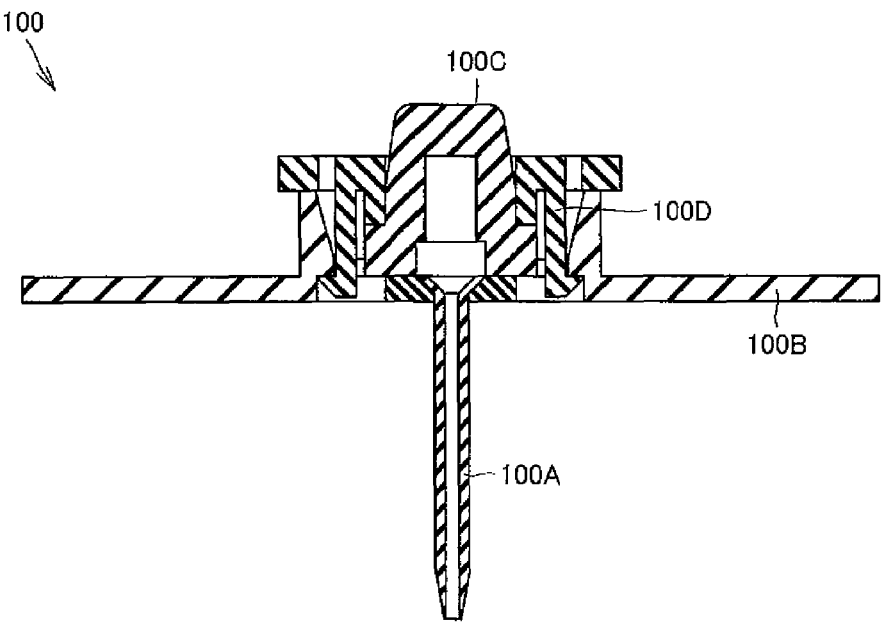
FIG. 14 is a cross-sectional view showing an indwelling member of an infusion device.

FIG. 14 is a cross-sectional view showing indwelling member 100 to be fixed on the body surface of the user by the inserter in the present embodiment. Indwelling member 100 forms a part of an infusion device used for continuous subcutaneous insulin infusion (CSII), and includes cannula 100A, a base 100B, a diaphragm 100C and a latch portion 100D. Here the infusion device is also applicable to any use for supplying a medical solution other than insulin into the body (such as pain treatment for example).

To indwelling member 100, a coupling member (not shown) is removably attached. From the coupling member, a medical solution is supplied into indwelling member 100.

As for cannula 100A, in order to adapt to movements in daily life in the state where the cannula is inserted in the body of the user, cannula 100A is preferably made of a resin having a certain degree of flexibility and a certain degree of strength (such as fluorine-contained resin, polyethylene, polypropylene or polyurethane for example).

Base 100B is directly fixed to the body of the user. On the lower surface of base 100B, an adhesive layer formed of a nonwoven cloth for example is provided.

Diaphragm 100C is made of a material having a certain degree of flexibility (such as natural rubber, synthetic polyisoprene rubber, butyl rubber, chloroprene rubber, silicon rubber, urethane rubber, styrene-butadiene rubber, ethylene-propylene rubber, acrylic rubber, fluorine-contained rubber, or thermoplastic elastomer for example). When the coupling member is attached to indwelling member 100, the coupling member extends through diaphragm 100C to reach the inner space of diaphragm 100C. Accordingly, a medical solution supplied from the coupling member is directed into the body of the user via cannula 100A.

Figure 15:
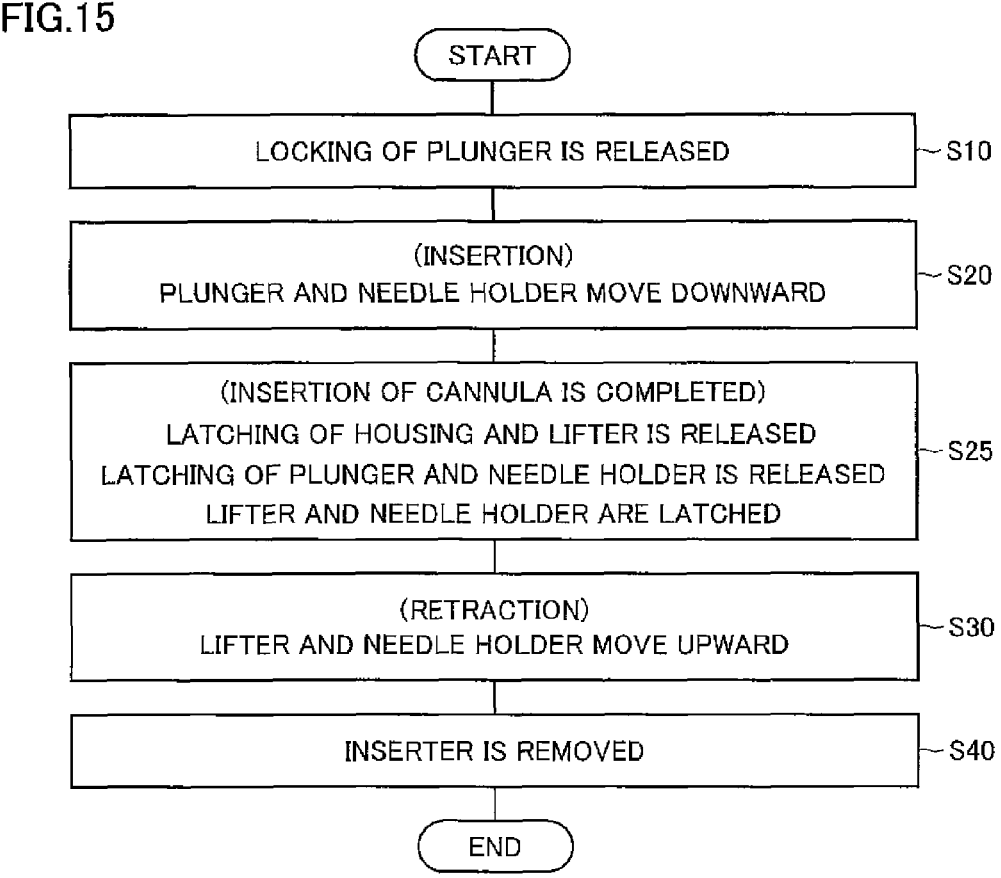
FIG. 15 is a flowchart illustrating an operation of the inserter according to an embodiment of the present invention.

Here, the operation of the inserter in the present embodiment will be summarized with reference to the flowchart in FIG. 15. First, in S10 ("step" is abbreviated as S), locking of plunger 10 is released. As a result, in S20, plunger 10 and needle holder 30 move downward (Insertion). Then, in S25, as the insertion of cannula 100A is completed, the latching of lifter 20 by housing 1 is released and the latching of needle holder 30 by plunger 10 is released, while needle holder 30 is latched by lifter 20. As a result, in S30, lifter 20 and needle holder 30 move upward. After the retraction in S30 is completed, the inserter is removed in S40.

The inserter in the present embodiment has, as described above, the capability of automatically inserting cannula 100A and the capability of automatically retracting insertion needle 40, so that both of the advantage of facilitating the insertion of cannula 100A by the user and the advantage of suppressing accidental puncture by insertion needle 40 can be achieved. Further, the above-described automatic insertion capability and automatic retraction capability can be accomplished with one spring 50 and thus the inserter that is convenient to use can be provided while avoiding an increase of the number of parts.

In summary, the inserter in the present embodiment is an inserter for automatically inserting cannula 100A of indwelling member 100 of an infusion device into the body of a user, and includes: tubular housing 1; plunger 10 serving as "first member" contained in housing 1 in a state where the plunger is movable in an axial direction and holding indwelling member 100; lifter 20 serving as "second member" provided on a side opposite to a body surface of the user with respect to plunger 10, contained in housing 1 in a state where the lifter is relatively movable in the axial direction relative to plunger 10, and having flange portion 21 serving as "first latch portion" that can be latched by housing 1; needle holder 30 serving as "third member" contained in housing 1 and having projection 31 serving as "second latch portion" that can be latched by plunger 10 and lifter 20; insertion needle 40 held by needle holder 30 and inserted in cannula 10A; and spring 50 serving as "biasing member" provided between plunger 10 and lifter 20 and applying a biasing force in a direction of biasing plunger 10 and lifter 20 away from each other.

Before indwelling member 100 reaches the body surface of the user, flange portion 21 of lifter 20 is latched by housing 1 and projection 31 of needle holder 30 is latched by plunger 10.

The inserter is provided with hook portion 11A serving as "latch release portion" that releases latching of flange portion 21 of lifter 20 by housing 1 when indwelling member 100 reaches the body surface of the user, and hook portion 22 serving as "latch switch portion" that releases latching of projection 31 of needle holder 30 by plunger 10 when indwelling member 100 reaches the body surface of the user and causes projection 31 of needle holder 30 to be latched by lifter 20.

More specifically, lifter 20 has flange portion 21, and housing 1 has projection 1C serving as "flange abutting portion" abutting on the rim of flange portion 21. Hook portion 11A serves as "press portion" pressing projection 1C radially outward when indwelling member 100 reaches the body surface of the user. Thus, hook portion 11A serves as "latch release portion."

Projection 31 is formed to protrude radially outward so that the projection can be latched by plunger 10. Needle holder 30 has tapered surface 32 inclining from an upper side toward a lower side in the direction from the radial outside toward the radial inside. When indwelling member 100 reaches the body surface of the user, hook portion 22 serves as "taper abutting portion" abutting on tapered surface 32 to deform needle holder 30 so that projection 31 is moved radially inward. Thus, hook portion 22 serves as "latch switch portion" so that projection 31 of needle holder 30 is latched by hook portion 22 of lifter 20.

Figure 16:
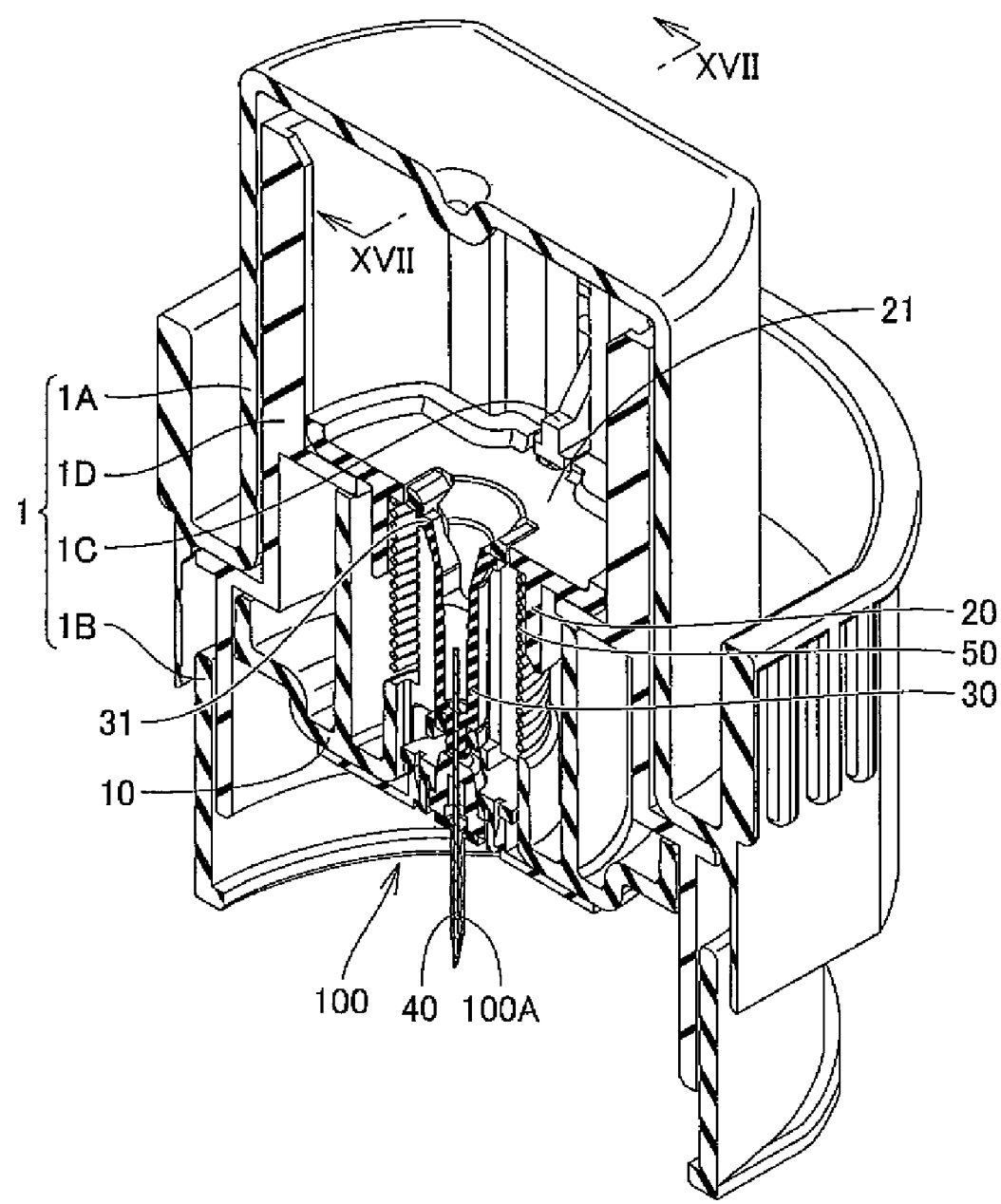
FIG. 16 is a perspective cross-sectional view showing a modification of the inserter according to an embodiment of the present invention.
Figure 17:
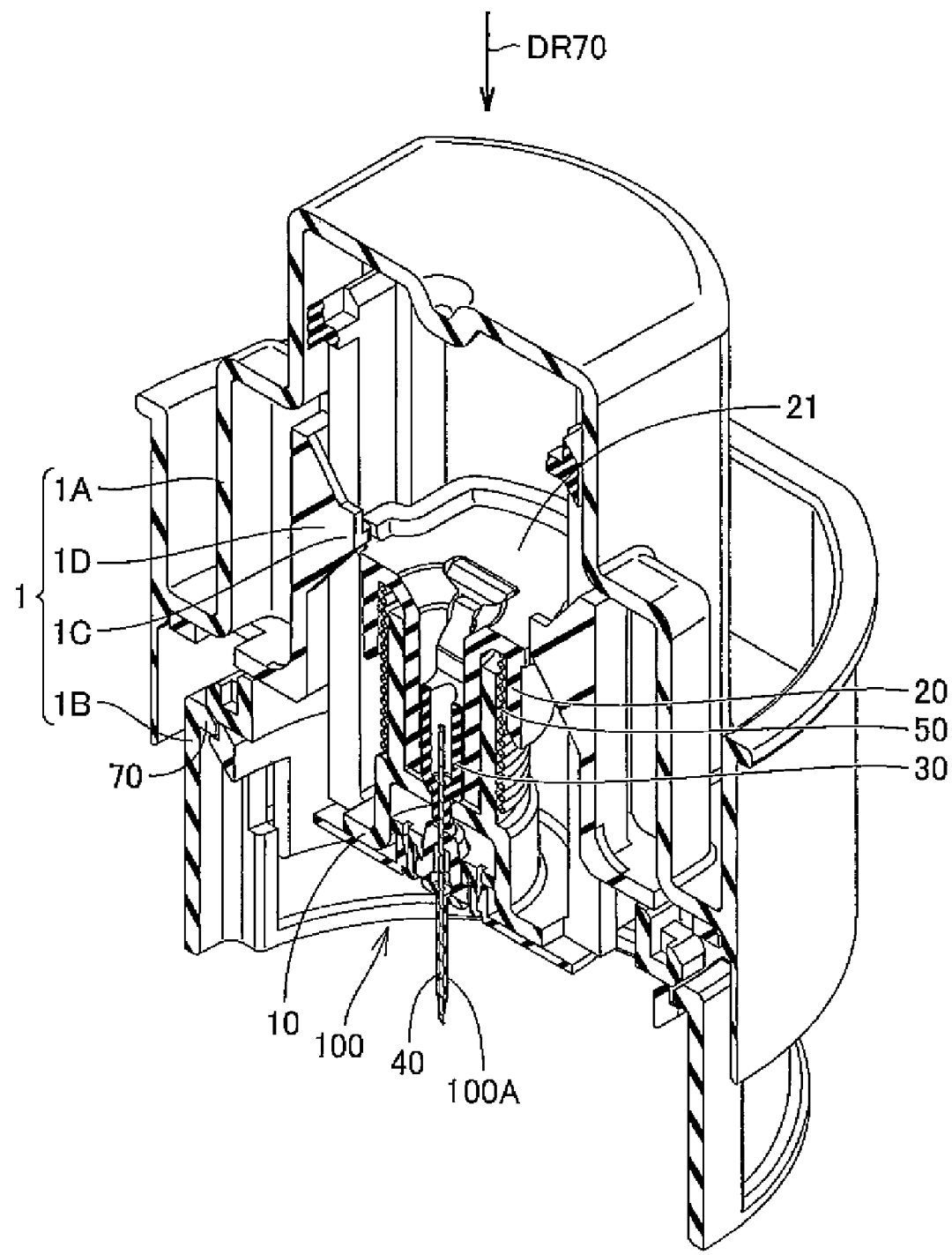
FIG. 17 is a perspective cross-sectional view corresponding to the XVII-XVII cross section in FIG. 16.

In the following, a modification of the inserter in the present embodiment will be described with reference to FIGS. 16 to 21. FIG. 16 is a perspective cross-sectional view showing an inserter in the present modification, and FIG. 17 is a perspective cross-sectional view corresponding to the XVII-XVII cross section in FIG. 16. Referring to FIGS. 16 and 17, in the inserter of the present modification, an intermediate member 1D is provided between upper member 1A and lower member 1D, and projection 1C engaging with flange portion 21 of lifter 20 is provided at intermediate member 1D.

The inserter in the present modification has a feature that locking of plunger 10 is released by pressing upper member 1A toward the body surface of the user (namely in the direction indicated by arrow DR70). Specifically, in the initial stage, plunger 10 is locked by lock portion 70 formed at lower member TB. Upper member 1A is pressed in the direction of arrow DR70 so that locking by lock portion 70 is released and the automatic insertion of indwelling member 100 by means of the biasing force of spring 50 is started.

Figure 18:
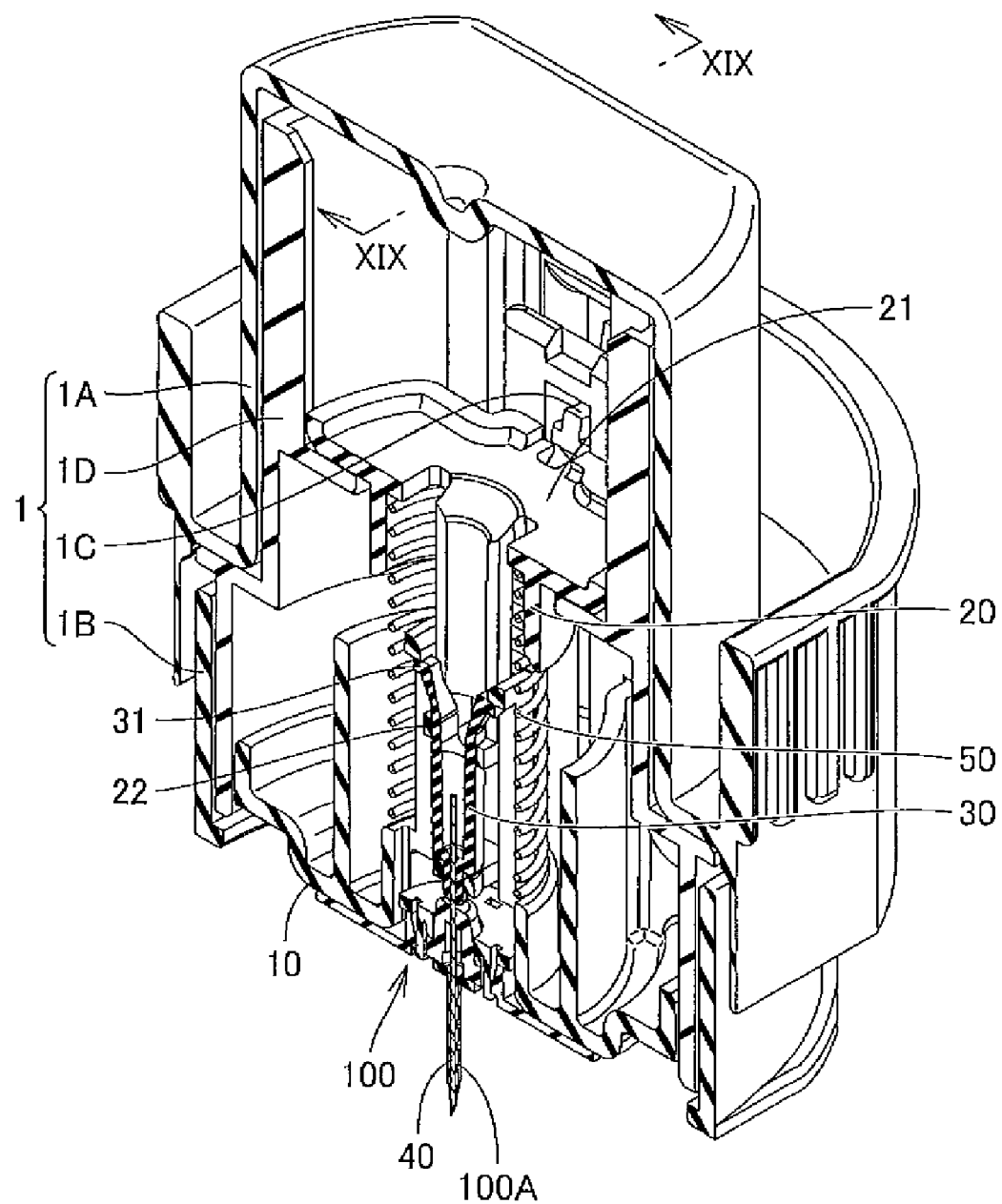
FIG. 18 is a perspective cross-sectional view showing an intermediate stage of the insertion according to a modification of the inserter in an embodiment of the present invention.
Figure 19:
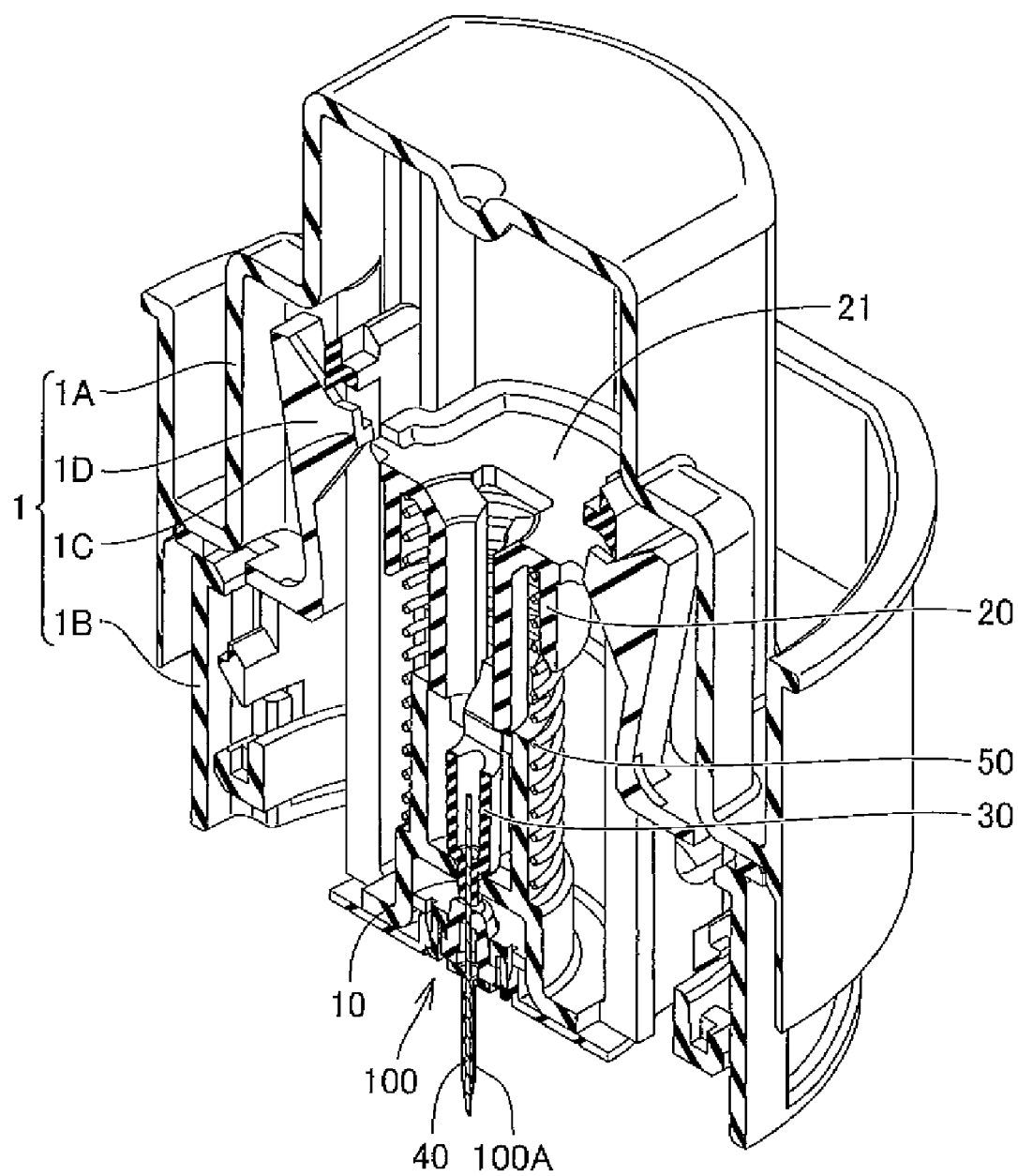
FIG. 19 is a perspective cross-sectional view corresponding to the XIX-XIX cross section in FIG. 18.
Figure 20:
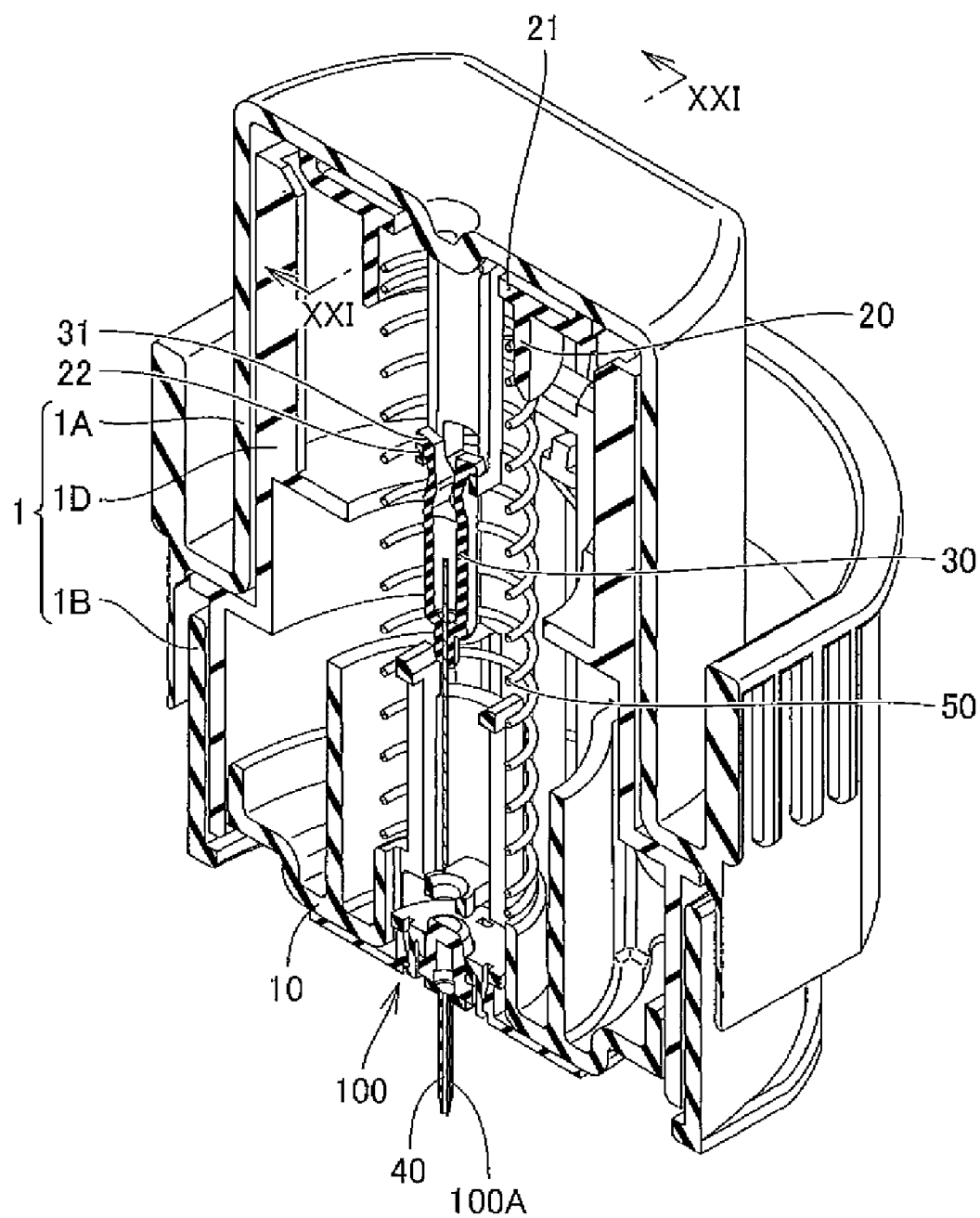
FIG. 20 is a perspective cross-sectional view showing a state after the retraction of an insertion needle is completed according to a modification of the inserter in an embodiment of the present invention.
Figure 21:
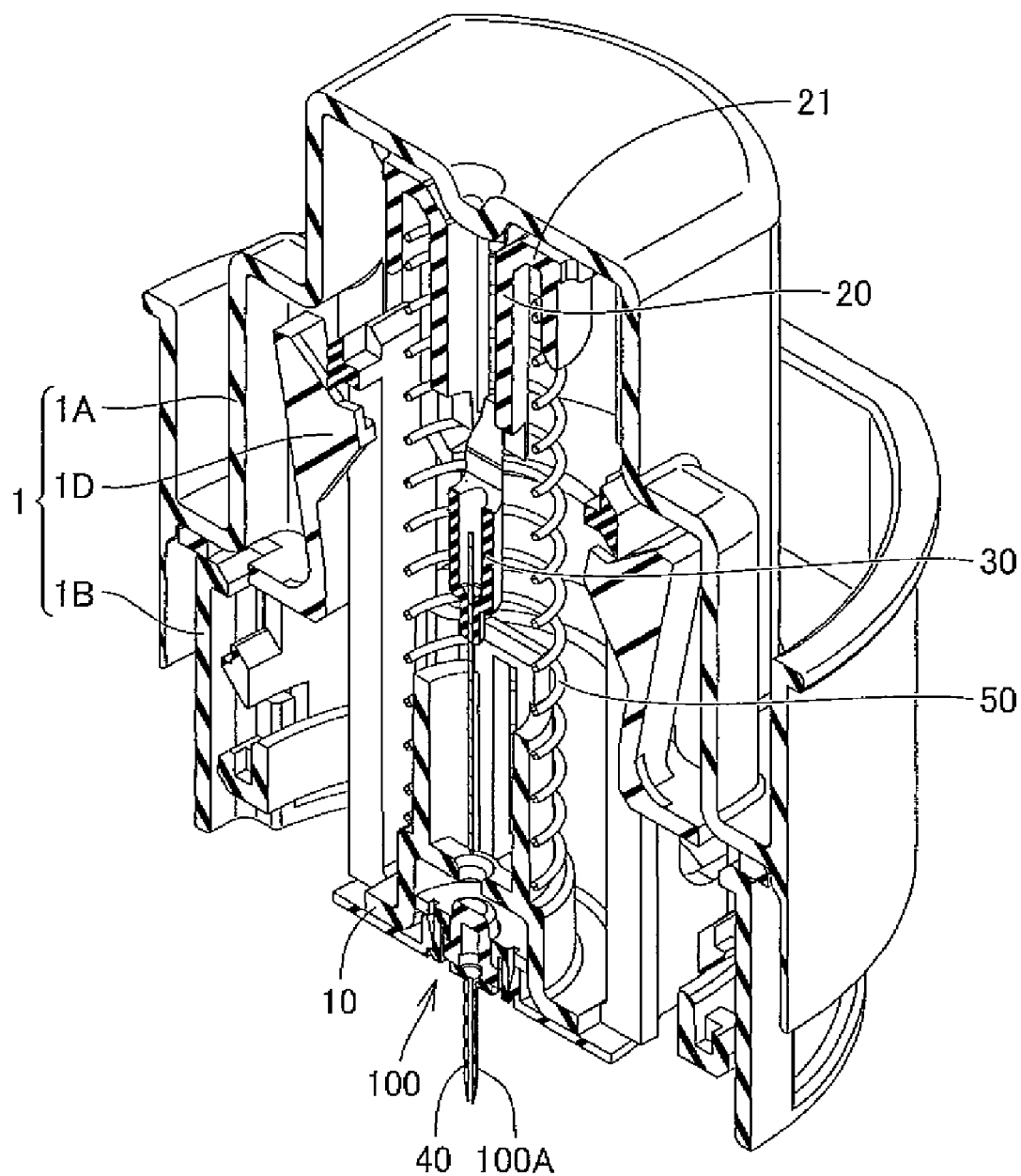
FIG. 21 is a perspective cross-sectional view corresponding to the XXI-XXI cross section in FIG. 20.

FIG. 18 is a perspective cross-sectional view showing an intermediate stage of the insertion of the inserter in the present modification, and FIG. 19 is a perspective cross-sectional view corresponding to the XIX-XIX cross section in FIG. 18. FIG. 20 is a perspective cross-sectional view after the retraction of the insertion needle in the inserter of the present modification is completed, and FIG. 21 is a perspective cross-sectional view corresponding to the XXI-XXI cross section in FIG. 20.

As shown in FIGS. 18 and 19, before indwelling member 100 reaches the body surface of the user, flange portion 21 of lifter 20 is latched by projection 1C and projection 31 of needle holder 30 is latched by plunger 10.

Then, as indwelling member 100 reaches the body surface of the user, a mechanism similar to that of the inserter shown in FIGS. 1 to 14 causes the latching of flange portion 21 of lifter 20 by projection 1C and the latching of projection 31 of needle holder 30 by plunger 10 to be released and causes projection 31 of needle holder 30 to be latched by lifter 20. Accordingly, as shown in FIGS. 20 and 21, the biasing force of spring 50 can be used to move lifter 20 and needle holder 30 upward.

As seen from the above, the inserter that starts the insertion by pressing housing 1 from above also automatically retracts the insertion needle so that accidental puncture by the insertion needle can be suppressed.

Although the present invention has been described and illustrated in detail, it is clearly understood that the same is by way of illustration and example only and is not to be taken by way of limitation, the scope of the present invention being interpreted by the terms of the appended claims.

What is claimed is:

1. An inserter for automatically inserting a cannula of an indwelling member of an infusion device into a body of a user, comprising:
    a tubular housing;
    a first member contained in said housing in a state where said first member is movable in an axial direction and holding said indwelling member;
    a second member provided on a side opposite to a body surface of said user with respect to said first member, contained in said housing in a state where said second member is relatively movable in the axial direction relative to said first member, and having a first latch portion that can be latched by said housing;
    a third member contained in said housing and having a second latch portion that can be latched by said first member and said second member;
    an insertion needle held by said third member and inserted in said cannula; and
    a biasing member provided between said first member and said second member and applying a biasing force in a direction of biasing said first member and said second member away from each other, wherein
    before said indwelling member reaches the body surface of said user, said first latch portion of said second member is latched by said housing and said second latch portion of said third member is latched by said first member,
    a latch release portion is provided that releases latching of said first latch portion of said second member by said housing when said indwelling member reaches the body surface of said user, and
    a latch switch portion is provided that releases latching of said second latch portion of said third member by said first member when said indwelling member reaches the body surface of said user and causes said second latch portion of said third member to be latched by said second member.

2. The inserter according to claim 1, wherein
said second member has a flange portion,
said housing has a flange abutting portion abutting on a rim of said flange portion,
said first member has a press portion pressing said flange abutting portion radially outward when said indwelling member reaches the body surface of said user,
said first latch portion includes said flange portion, and
said latch release portion includes said press portion.

3. The inserter according to claim 1, wherein
said third member has a projection that protrudes radially outward and can be latched by said first member, and a taper portion whose diameter gradually decreases from an upper side toward a lower side,
said second member has a taper abutting portion abutting on said taper portion when said indwelling member reaches the body surface of said user to deform said third member such that said projection is moved radially inward,
said second latch portion includes said projection, and
said latch switch portion includes said taper abutting portion.

4. The inserter according to claim 3, wherein
said taper abutting portion of said second member latches said projection of said third member.

5. The inserter according to claim 1, wherein
a lock mechanism is provided that is disposed on a side surface of said housing and locks said first member on said housing against the biasing force of said biasing member, and
said lock mechanism is released by pressing a button protruding from the side surface of said housing.

* * * * *